US011083599B1

(12) United States Patent
Churchill

(10) Patent No.: US 11,083,599 B1
(45) Date of Patent: Aug. 10, 2021

(54) GENITAL COVER

(71) Applicant: Cole Patrick Churchill, Mt. Prospect, IL (US)

(72) Inventor: Cole Patrick Churchill, Mt. Prospect, IL (US)

(*) Notice: Subject to any disclaimer, the term of this patent is extended or adjusted under 35 U.S.C. 154(b) by 107 days.

(21) Appl. No.: 16/445,328

(22) Filed: Jun. 19, 2019

Related U.S. Application Data

(60) Provisional application No. 62/687,354, filed on Jun. 20, 2018.

(51) Int. Cl.
*A61F 2/50* (2006.01)
*A41D 13/00* (2006.01)

(52) U.S. Cl.
CPC ........ *A61F 2/50* (2013.01); *A61F 2002/5001* (2013.01)

(58) Field of Classification Search
CPC ................ A61F 2/50; A61F 2002/5001; A61F 2002/5003; A61F 2002/5007
See application file for complete search history.

(56) References Cited

U.S. PATENT DOCUMENTS

| | | | | |
|---|---|---|---|---|
| 849,471 A | * | 4/1907 | Gamble | A63B 71/1216 602/72 |
| 2,283,684 A | * | 5/1942 | Matthews | A63B 71/12 602/72 |
| 3,229,692 A | * | 1/1966 | Creed | A63B 71/08 602/72 |
| 3,788,314 A | * | 1/1974 | Noreen | A63B 71/1216 602/67 |
| D246,011 S | * | 10/1977 | Eckman | D2/711 |
| 4,134,400 A | * | 1/1979 | DiMatteo | A61F 5/40 602/72 |
| D252,116 S | * | 6/1979 | DiMatteo | D2/711 |
| 4,257,414 A | * | 3/1981 | Gamm | A63B 71/1216 602/67 |
| 4,471,772 A | * | 9/1984 | Miller, Jr. | A61F 5/41 2/403 |
| 4,627,111 A | * | 12/1986 | Storie | A41B 9/005 2/69 |
| D294,075 S | * | 2/1988 | Bernstein | D2/711 |
| 4,967,768 A | * | 11/1990 | Tatro | A41B 9/02 128/891 |
| 5,285,531 A | * | 2/1994 | Nalbandian | A41B 9/04 2/106 |
| 5,405,312 A | * | 4/1995 | Jacobs | A41D 13/0568 128/892 |
| D364,262 S | * | 11/1995 | Magidson | D2/711 |

(Continued)

*Primary Examiner* — Robert H Muromoto, Jr.
(74) *Attorney, Agent, or Firm* — McDonnell Boehnen Hulbert & Berghoff LLP

(57) ABSTRACT

A genital cover for a transgender human which is positioned underneath clothing along the curve of the mons pubis/and or genitals which when worn gives the outward simulated appearance of the protruding bulge and contours of the human male external genitalia to provide the wearer who does not possess external male genitalia the subtle appearance of possessing external male genitalia; the genital cover itself does not resemble explicit external male genitalia when viewed unobstructed by clothing when worn; when worn beneath clothing the genital cover gives the simulated appearance of external male genitalia.

13 Claims, 13 Drawing Sheets

(56) References Cited

U.S. PATENT DOCUMENTS

| | | | | |
|---|---|---|---|---|
| 5,479,942 | A * | 1/1996 | DiMatteo | A61F 5/40 |
| | | | | 128/846 |
| 5,483,705 | A * | 1/1996 | DiMatteo | A63B 71/12 |
| | | | | 2/2.5 |
| 5,557,804 | A * | 9/1996 | Ovortrup | A41D 13/0506 |
| | | | | 128/888 |
| 5,819,323 | A * | 10/1998 | Edenfield | A41B 9/02 |
| | | | | 2/466 |
| 6,319,219 | B1 * | 11/2001 | Landi | A63B 71/12 |
| | | | | 128/846 |
| 7,178,176 | B1 * | 2/2007 | S-Cronenbold | A41D 1/088 |
| | | | | 2/403 |
| 7,757,310 | B2 * | 7/2010 | Wong | A41D 1/089 |
| | | | | 2/466 |
| D732,745 | S * | 6/2015 | Stewart | D29/101.5 |
| 9,211,211 | B2 * | 12/2015 | Maurette | A61F 2/50 |
| 9,526,969 | B1 * | 12/2016 | Raber | A41D 13/05 |
| 9,854,850 | B2 * | 1/2018 | Rana | A41B 9/04 |
| 10,540,911 | B2 * | 1/2020 | Cowperthwait | G09B 23/288 |
| 2003/0163076 | A1 * | 8/2003 | Lukens | G09F 21/02 |
| | | | | 602/67 |
| 2004/0154079 | A1 * | 8/2004 | Rana | A41B 9/004 |
| | | | | 2/406 |
| 2005/0278839 | A1 * | 12/2005 | Atwater, V | A63B 71/12 |
| | | | | 2/466 |
| 2006/0052031 | A1 * | 3/2006 | Parpia | A63H 3/24 |
| | | | | 446/304 |
| 2011/0190574 | A1 * | 8/2011 | Maurette | A61F 5/41 |
| | | | | 600/38 |
| 2017/0372639 | A1 * | 12/2017 | Cowperthwait | G09B 23/303 |

* cited by examiner

GENITAL COVER

CROSS-REFERENCE TO RELATED APPLICATION

This application claims priority to U.S. Provisional Patent Application No. 62/687,354, filed on Jun. 20, 2018, which is hereby incorporated by reference in its entirety.

FIELD OF THE INVENTION

This invention relates generally to transgender devices, and more particularly to an improved device for simulating the appearance of external male genitalia when worn underneath clothing, particularly by transgender men who possess external female genitalia.

BACKGROUND OF THE INVENTION

Genital covers, also called "packers," simulate the appearance of external male genitalia. These devices are therefore well known and widely utilized in the transgender male community, particularly for relieving the symptoms of gender dysphoria arising from the absence of male external genitalia. Because packers are used to benefit emotional health, said devices are typically worn daily and are often only removed when the wearer showers or sleeps.

Currently available genital covers are generally limited to the "prosthetic" or "penile prosthetic," which is a life-like sculpture or cast of the male phallus, often including the testicles. These prosthetics are typically rendered in silicone and secured in a jockstrap or other harness which wraps around the legs and/or abdomen, adhered to the skin through the use of glue or adhesives, or simply worn underneath clothing. Prosthetics are sometimes painted with realistic details to give the outward appearance of male genitalia. Such prosthetics normally have an unadorned rear side which rests against the wearer's abdomen or genital region. While the aid of a harness or skin adhesives are intended to limit the device from moving during daily wear, and particularly during moderate to intense physical activities, it is well understood in the transgender community that such devices can be uncomfortable and fail to remain in place. When worn for extended periods of time or during physical activity, it is common for the wearer to experience pain arising from the contact of the straps of the harness against the skin, or when external forces press the prosthetic into the wearer's body. Moreover, the use of adhesives or silicone-type "life-like" materials can result in skin irritation or the pulling/removal of hair, causing further discomfort.

Thus, there exists a need for a new and improved geometry for transgender genital covers that simulate the appearance of male external genitalia while being comfortable to wear by remaining in place without the need for harnesses or adhesives.

SUMMARY OF THE INVENTION

In one aspect, the present disclosure provides a genital cover that affords better stability and improved comfort in comparison to prior art devices. The genital cover has improved geometry that affords better stability, causing the cover to retain its proper position. The cover may also comprise a composition which compresses to reduce the possibility for having the device move under an applied external force.

In one embodiment, the genital cover comprises a front component including a substantially convex front surface, and a rear component including an ergonomic rear surface. The substantially convex front surface of the front component is designed to give the wearer the appearance of possessing male external genitalia. The ergonomic rear surface of the rear component is designed to rest along the mons pubis and genital region of the wearer and to have sufficient volume to fill the wearer's undergarments. To achieve these characteristics, both the substantially convex front surface of the front component and the ergonomic rear surface of the rear component may be substantially continuous along the front and rear of the cover, respectively.

In some embodiments, the genital cover may be made of one or more pieces, which may be combined together to form a single unit. For example, the cover may include a front component, wherein the rest of the cover is provided in one or more additional components. The front component may comprise different materials from the rest of the cover, which may differ density or firmness. For example, the cover may include a front component that is higher in density and firmness compared to the rest of the cover, so as to sufficiently retain its shape when force is exerted against the cover, thereby subtly suggesting that the wearer possesses external male genitalia.

In some embodiments, the genital cover may include a rear component, wherein the rest of the cover is provided in one or more additional components. The rear component may include contours that mimic the external contours of the mons pubis, thereby allowing the cover to fit ergonomically against the mons pubis and remain in place. The rear component may comprise different materials from the rest of the cover, which may differ density or firmness. For example, the cover may include rear component that is lower in density and firmness compared to the rest of the cover, so as to provide enhanced comfort and protect against injury or discomfort when excessive frontal force is exerted on the cover.

DETAILED DESCRIPTION

Figure 1:
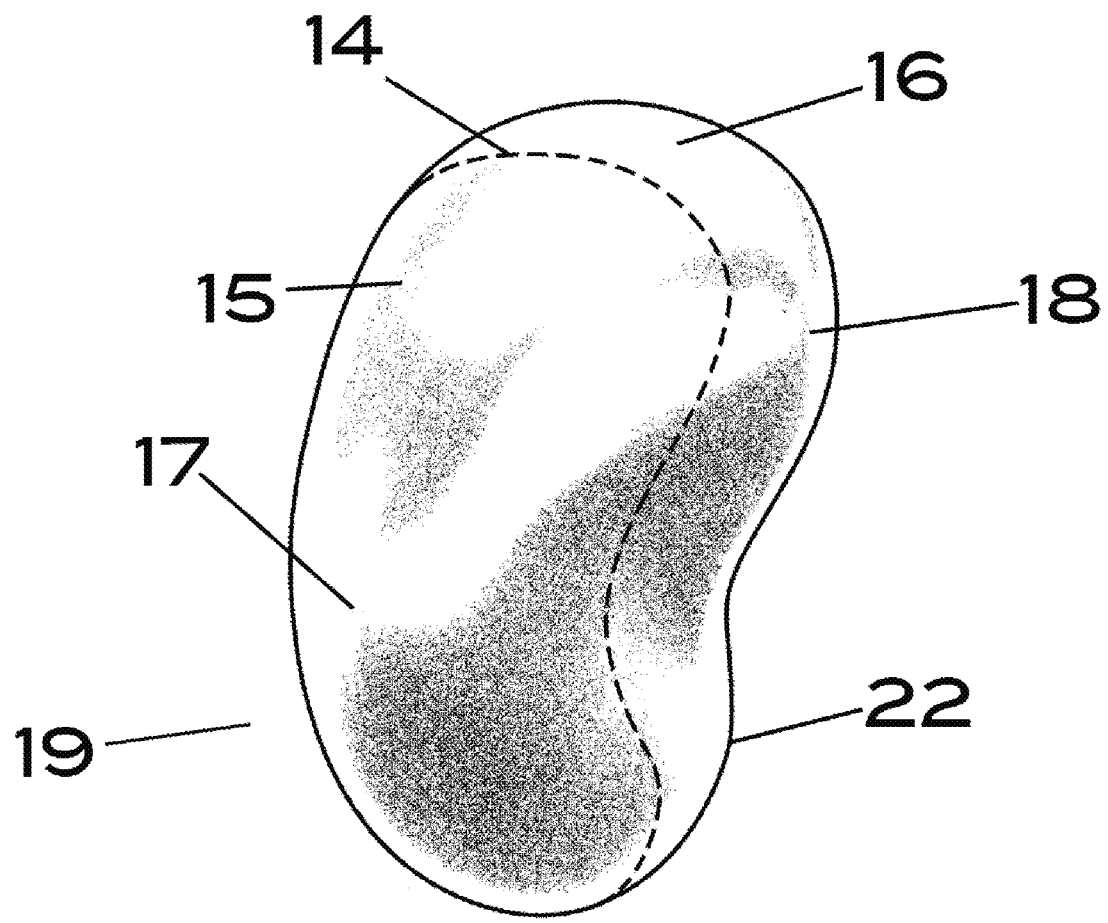
FIG. 1 illustrates a perspective view of a genital cover, according to an aspect of the present disclosure.

The following detailed description describes various features and functions of the disclosed methods, apparatus, and systems with reference to the accompanying figures. In the figures, similar symbols typically identify similar components, unless context dictates otherwise. The illustrative method, apparatus, and system embodiments described herein are not meant to be limiting. It will be readily understood that certain aspects of the disclosed methods, apparatus, and systems can be arranged and combined in a wide variety of different configurations, all of which are contemplated herein.

As used herein, the term "male external genitalia" is a collective term to describe the anatomical external human male genital region; the penis and scrotum associated with human male external genitalia.

As used herein, the term "female external genitalia" is a collective term to describe the anatomical external human female genital region; to include the clitoris and labia.

As used herein, the term "genitals" or "genitalia" but excluding "male external genitalia" are collective terms to describe any genitals which themselves do not produce the outward appearance of typical external male genitalia when beneath clothing, such as the clitoris and labia.

As used herein, the term "transgender man" in this application refers to any human assigned female at birth who does not currently possess male external genitalia who has a desire to possess male external genitalia and/or simulate the appearance of such.

In one aspect, the genital cover includes a substantially convex front surface, and an ergonomic rear surface. The substantially convex front surface is designed to give the wearer the appearance of possessing male external genitalia. The ergonomic rear surface is designed to rest along the mons pubis and genital region. The cover has sufficient volume to fill the wearer's undergarments and provide the appearance of male external genitalia.

The genital cover may include a single component or multiple components that combine to form a single unit. The cover may be placed inside the crotch portion of human pants, on the outer crotch portion of a human undergarment, or may be inserted into the space between an outer cloth layer and an inner cloth layer of an undergarment. But unlike the prosthetics known in the art, the genital cover possesses a geometry that makes the cover capable of being retained in its intended place without the use of harness or adhesive. As a result, the cover greatly reduces the undesirable movement that is common with previously described devices. The cover described herein is designed to remain in its intended place through daily activities, such as walking, standing or sitting, as well as intense athletic activities, such as running. This is a vast improvement over the currently available prosthetics, which do not possess geometry capable of retaining said device in its intended place without the use of harnesses or adhesives. As many transgender men have experienced, said unsecured devices move from their intended place through daily activities as simple as walking or moving from a standing to sitting position, and require constant adjustment. Moreover, during moderate to intense activities, such as running, said devices may shift so dramatically as to fall down the wearer's pant leg and require action to prevent onlookers from noticing the now exposed prosthetic, thereby discovering the wearer's status as a transgender individual. Thus, the stability of the cover disclosed herein provides the wearer with the reassurance that the cover will not be inadvertently exposed, thereby revealing the wearer's status as a transgender individual.

In some embodiments, the genital cover includes a single unit having a front component including a substantially convex front surface and a rear component including an ergonomic rear surface. In other embodiments, the front and rear components may be removably coupled, optionally with additional components, to form a single unit. For example, the cover may include a front component having a substantially convex front surface on the anterior surface of the front component, and a rear component having an ergonomic rear surface on the anterior side of the front component. In some embodiments, the front component and rear component may be combined by contacting the posterior side of the front component with the anterior side of the rear component. For example, an entirety of a posterior side of the front component may contact an entirety of an anterior side of the rear component to form the genital cover device.

The front component and rear component of the genital cover may be removably, coupled by a coupling mechanism, which may be selected depending on the materials included in the front component or rear component, as well as the intended use of the genital cover. The coupling mechanism may be selected from attachment methods known in the art, including, for example, mechanical fastener, hook and loop material or derivation thereof, magnets, adhesive, van der Waals forces, material surrounding the front and rear component to hold them together, or a combination thereof. In some embodiments, the coupling mechanism is material surrounding the front and rear component to hold them together, such as, for example, an elastic or semi-elastic material which may be in the shape of a band or a sock.

The substantially convex front surface may include an outward extension volume which may give the wearer the simulated appearance of the outward bulge and contours of the human male external genitalia. This provides the transgender man who does not possess external male genitalia the subtle appearance of possessing external male genitalia when viewed on the outer crotch surface of the wearer's garments, including undergarments, outer clothing of every-day dress or casual usage, swimsuits, close-fitting clothing, or any clothing worn outside the genital cover.

Currently available devices are often comprised of a single material with a single density or firmness throughout the device's entirety, normally silicone, which in varying prior art can range from extremely squishy and stretchy to moderately dense. While these different compositions may offer benefit in certain situations, such as extreme pliability preventing discomfort when the prosthetic is compressed against the body, such device only comprising of a single density throughout limits its ability to perform reliably in a larger range of situations encountered through daily and athletic use, each of which cause differing variances of compression and which require varying softness or firmness. Thus, in contrast to the known devices, the genital cover disclosed herein may be made of one or more pieces, which may be combined together to form a single unit.

For example, the cover may include a front component, wherein the rest of the cover includes one or more additional components. The front component may comprise different materials from the rest of the cover, which may have different density or firmness. For example, the cover may include a substantially convex front component that is higher in density and firmness compared to the rest of the cover, so as to sufficiently retain its shape when force is exerted against the cover, thereby subtly suggesting that the wearer possesses external male genitalia. In some embodiments, the front component may also include a convex outward extension volume, designed to provide maximum comfort for the wearer and to simulate the size and shape of clothed male external genitalia. In other embodiments, the front component includes a lower extending portion that is preferably thinner than the upper portion of the cover. The lower extending portion is shaped to not impede the forward movement of the wearer's legs, and has a width and shape that emulates the contours of clothed male external genitalia.

In some embodiments, the genital cover may include a rear component, wherein the rest of the cover includes one or more additional components. The rear component may include contours that mimic the external contours of the mons pubis, thereby allowing the cover to fit ergonomically against the mons pubis. In some embodiments, the rear component includes a depression of sufficient length and depth to accommodate the female external genitalia of the wearer. The rear component may also include bilateral outward extending edges that compress against the legs and aid in keeping the cover in place during movement. In some embodiments, the cover includes a bulbous protrusion on the lower part of the posterior side of the rear component, and slightly concave area on the posterior surface of the upper part of the rear component. The slightly concave area on the upper rear surface is shaped to contact the mons pubis, and the lower bulbous protrusion on the lower area provides contact with the lower genital region, which provides resistance against upward force exerted on the genital cover. In some embodiments, the lower bulbous protrusion does not extend outward along the length of the genital region. The rear component may also comprise different materials from the rest of the cover, which may have different density or firmness.

The materials included in the front and rear components may be selected to accommodate the different functions of the front and rear components. In some embodiments, the front component may include a first material, and the rear component may include a second material. In some embodiments, the first material may include different materials from the rest of the cover, which may have different density or firmness. In other embodiments, the second material may include different materials from the rest of the cover, which may have different density or firmness. For example, the front component may include a first material that is different (e.g., more dense) than the second material of the rear component.

The material on the surface of the front and rear components may also differ from the material on the interior or core of the component. For example, the component may have a surface material or cover that is soft or has a high coefficient of friction for better adherence to outside forces. In some embodiments, the material of the posterior side of the front component may differ from other materials in the front component for better coupling to the anterior side of the rear component. Likewise, the material of the anterior side of the rear component may differ from other materials in the rear component for better coupling to the posterior side of the front component.

The materials of the cover may be selected from materials known in the art. For example, the cover may include plastics such as polypropylene, high-density polyethylene, low-density polyethylene, vinyl polyethylene, vinyl acetate and derivatives thereof, silicone, cloth, cotton, polyester, natural rubber, ethylene-vinyl acetate (EVA) foam, viscoelastic polyurethane foam, low-resilience polyurethane foam (memory foam) or flexible polyurethane foam. The front and rear component may each include more than one individual material, or a combination of materials (e.g., a plastic copolymer or a polyester/cotton blend). In one embodiment, the front and rear components include the same material, while in other embodiments, the front and rear components include different materials. In some embodiments, the front component includes a more rigid material, such as EVA foam. In other embodiments, the rear component includes a softer material, such as memory foam. In some embodiments, the front and rear components both include EVA foam but of different densities/softness. For example, the front component and rear component may both include EVA, but the front component includes a denser EVA than the rear component. Likewise, in some embodiments, the front and rear components both include polyurethane but of different densities/softness. For example, the front component and rear component may both include polyurethane, but the front component includes a denser polyurethane than the rear component. In other embodiments, the front and rear components may include any combination EVA foam memory foam and polyurethane.

In one embodiment, the genital cover includes a substantially convex front surface, and an ergonomic rear surface, wherein the substantially convex front surface includes a convex outward extension having a volume simulating male external genitalia, and the ergonomic rear surface comprises contours that allow the cover to fit ergonomically against the mons pubis of a transgender man. The genital cover may be made of a single component or multiple components combined together to form a single unit, wherein the components may be of different densities and firmness. When made of multiple pieces, the outer convex front component may be higher in density and firmness compared to the rest of the cover so as to sufficiently retain its shape when force is exerted against the cover, so as to subtly suggest that the wearer possesses external male genitalia. The rear contours of the front component may mimic the external contours of the mons pubis, so that the cover fits ergonomically against the mons pubis. The rear component may be softer on the inside and along the edges to provide comfort to the wearer when excessive frontal force is exerted on the cover, through, for example, daily movements such as walking, biking, climbing stairs, or other physical activities where the movement of the legs causes any amount of force to be exerted against the cover. The rear portion of the cover may be softer and compress more easily than the front component and may also aid in keeping the cover in its intended place upon impact with the body or an external Object. In some embodiments, the cover is larger at the top than at the bottom, resulting in the shape of an upside down triangle with rounded corners. The lower convex portion on the rear component may curve outward in a bulbous shape to provide sufficient resistance to upward movement when force is exerted on the cover from below, said convex protrusion then curves away from the genital region so as to prevent unwanted genital contact with the cover while wearing. The cover may be comprised of lightweight materials such as foam to promote the cover remaining in its intended place due to the reduction of gravitational forces pulling the cover downward.

The contours of the rear component provide enhanced comfort to the wearer, and protect against injury or discomfort when excessive frontal force is exerted on the cover.

When forces are exerted on the cover so as to press said cover against the wearer's body, the rear component may be comprised of a material that allows it to be compressed. In some embodiments, the rear component is softer in the inside and along the edges to provide comfort to the wearer through daily movements in which the movement of the legs causes any amount of force to be exerted against the cover, such as walking, biking, climbing stairs, etc. The rear portion of the cover is softer and compresses more easily than the front so as to absorb impact resulting from contact with the body and environment and to keep the cover in its intended place. This provides comfort for the wearer despite pressure exerted upon said cover when pressed against the body, such as against the genitals or legs through movements brought about through daily wear. The cover fits ergonomically along the mons pubis and genital area as well as the inside of the legs as it is larger at the top in the shape of an upside down triangle with rounded corners so as to rest against the legs and be held in place. The lower convex portion on the rear curves outward in a bulbous shape to provide sufficient resistance to upward movement when force is exerted on the cover from below; said convex protrusion then curves away from the genital region so as to prevent unwanted genital contact with the cover while wearing. The cover when comprised of lightweight materials such as foam promotes the cover remaining in its intended place due to the reduction of gravitational forces pulling the cover downward.

Another shortcoming of the known devices is that many are designed to unmistakably look like external male genitalia when unobscured by clothing. As many transgender men have experienced, however, this unmistakably recognizable appearance may be detrimental to keeping their identity secret or avoiding embarrassing/uncomfortable situations. In many situations, it is dangerous for transgender individuals to have their identity discovered by others. Most prior art prosthetics can clearly be identified as phallus-like, and may prompt the discovery of the wearer's identity if unintentionally seen by others. Furthermore, this appearance is often not considered child-appropriate by parents or therapists who are in the position to provide said devices for transgender children, thereby preventing transgender children who may emotionally benefit from their use the opportunity to use them. Thus, the genital cover provided herein may have an inexplicit design to reduce the likelihood of unfavorable consequences arising from outsiders seeing said device unobstructed and to provide child-appropriate options.

Figure 2:
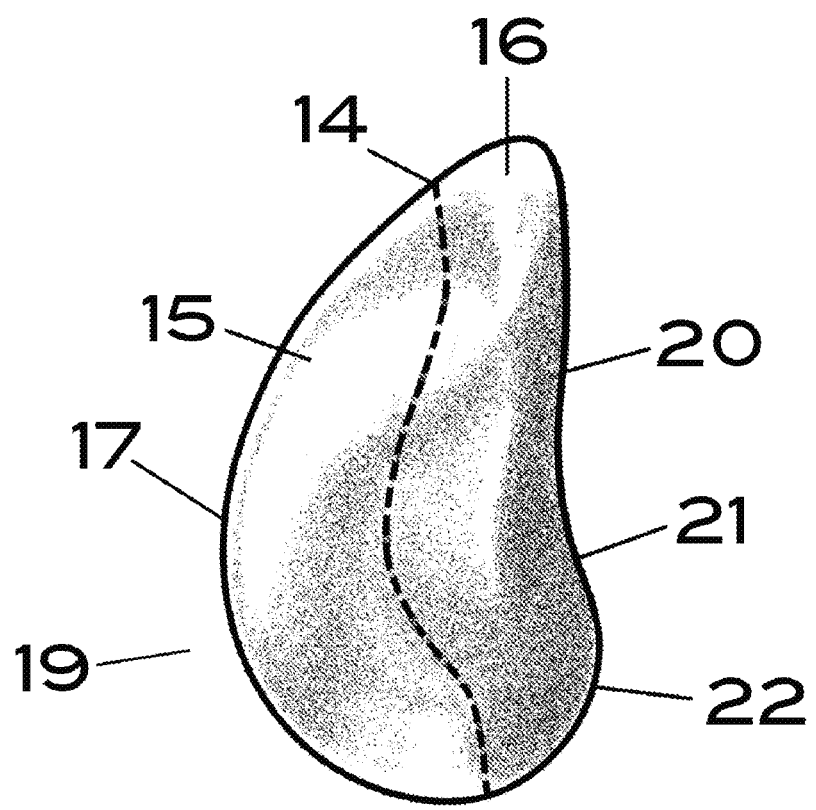
FIG. 2 illustrates a right side view of a genital cover, according to an aspect of the present disclosure.
Figure 3:
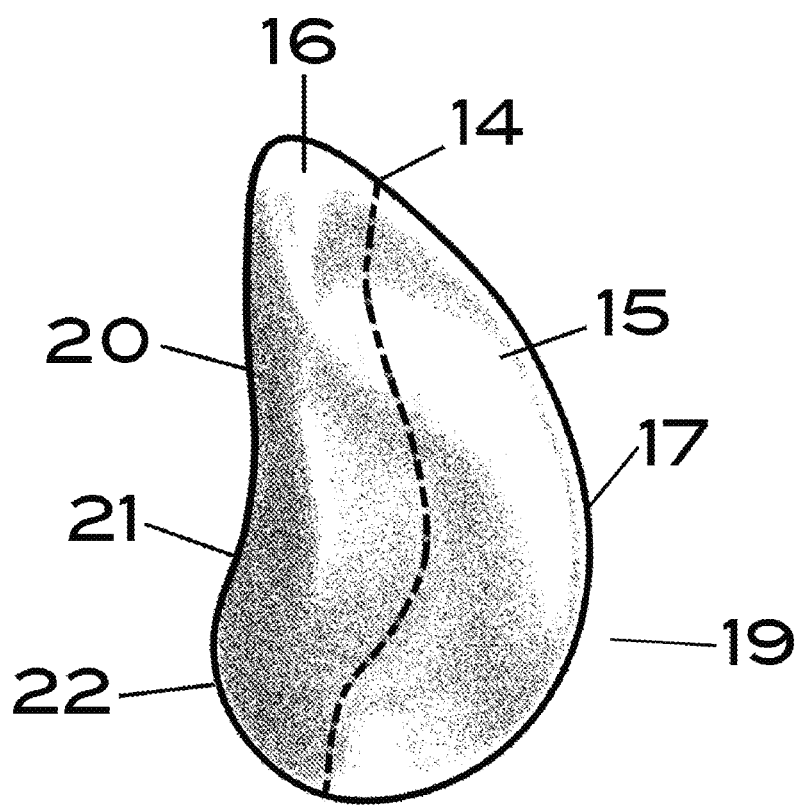
FIG. 3 illustrates a left side view of a genital cover, according to an aspect of the present disclosure.

FIGS. 1-7 illustrate the genital cover of this invention that is a single component cover or a multiple component cover in full assembly, while FIGS. 10-13 illustrate the genital cover before assembly or combination. As shown in FIGS. 2 and 3, the parting line 14 between the front component 15 and the rear component 16 preferably follows the curve of the convex outward extension volume 17, so as to leave ample area for the rear component 16. In some embodiments where the genital cover includes a single component, the parting line 14 is not present. In other embodiments, the cover optionally includes additional components, which may include a layer of material between the front component 15 and the rear component 16, on the concave front surface or on the ergonomic rear surface. Both single component and multiple component embodiments of the present invention are worn in identical positions and shown in FIGS. 8 and 9.

Figure 8:
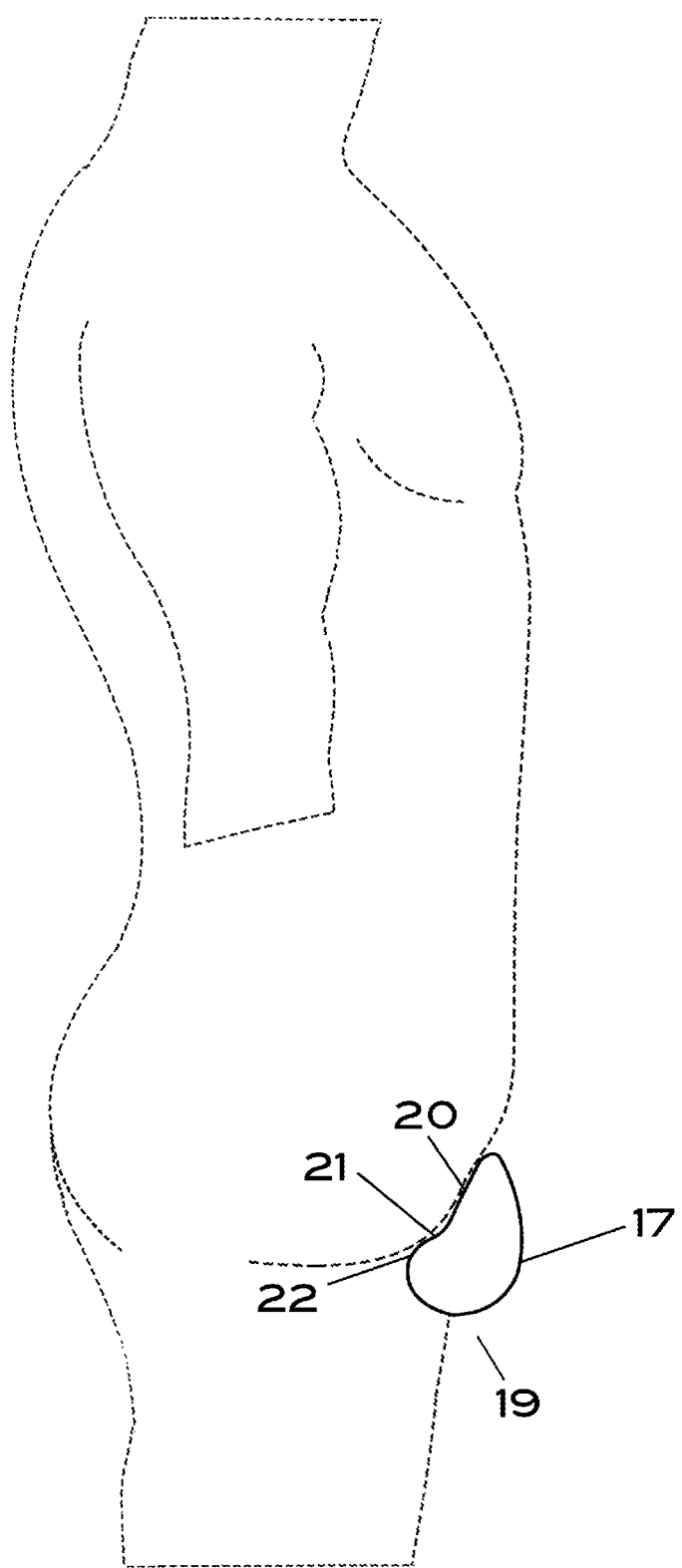
FIG. 8 illustrates a left side view of a genital cover, showing its intended position when worn by a transgender man, according to an aspect of the present disclosure.

In some embodiments, the rear surface may be comprised of a soft and easily compressible material, which would be comfortable resting against the upper legs and along the mons pubis, as shown in FIG. 8. The composition of the concave front component 15 may be comprised of a denser material than the composition of the ergonomic rear component 16, so as to give and resist at a level comparable to that of the male external genitalia when force is enacted against the concave front component 15, while also providing the benefit of subtly suggesting that the transgender wearer possesses male external genitalia. The parting line 14 can be placed in any arrangement, such as a straight vertical line, and can also be placed so as to redistribute the area ratio of the concave front component 15 to the ergonomic rear component 16. In some embodiments, the parting line may follow the outer curvature of the convex outward extension volume 17, Such an arrangement may provide maximum comfort and allow the concave front component 15 to extend along the length of the simulated male external genitalia.

Figure 4:
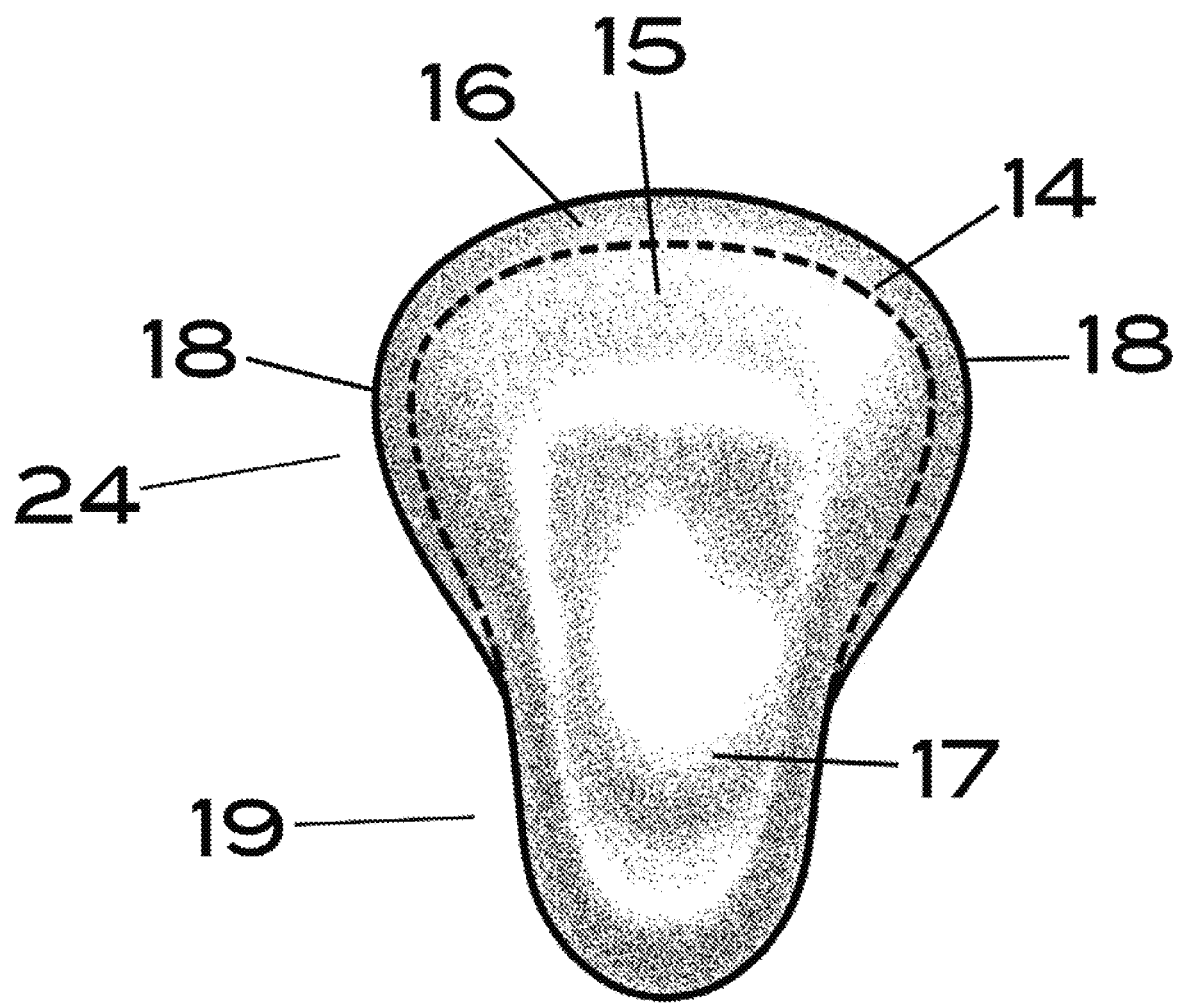
FIG. 4 illustrates a front side view of a genital cover, according to an aspect of the present disclosure.
Figure 5:
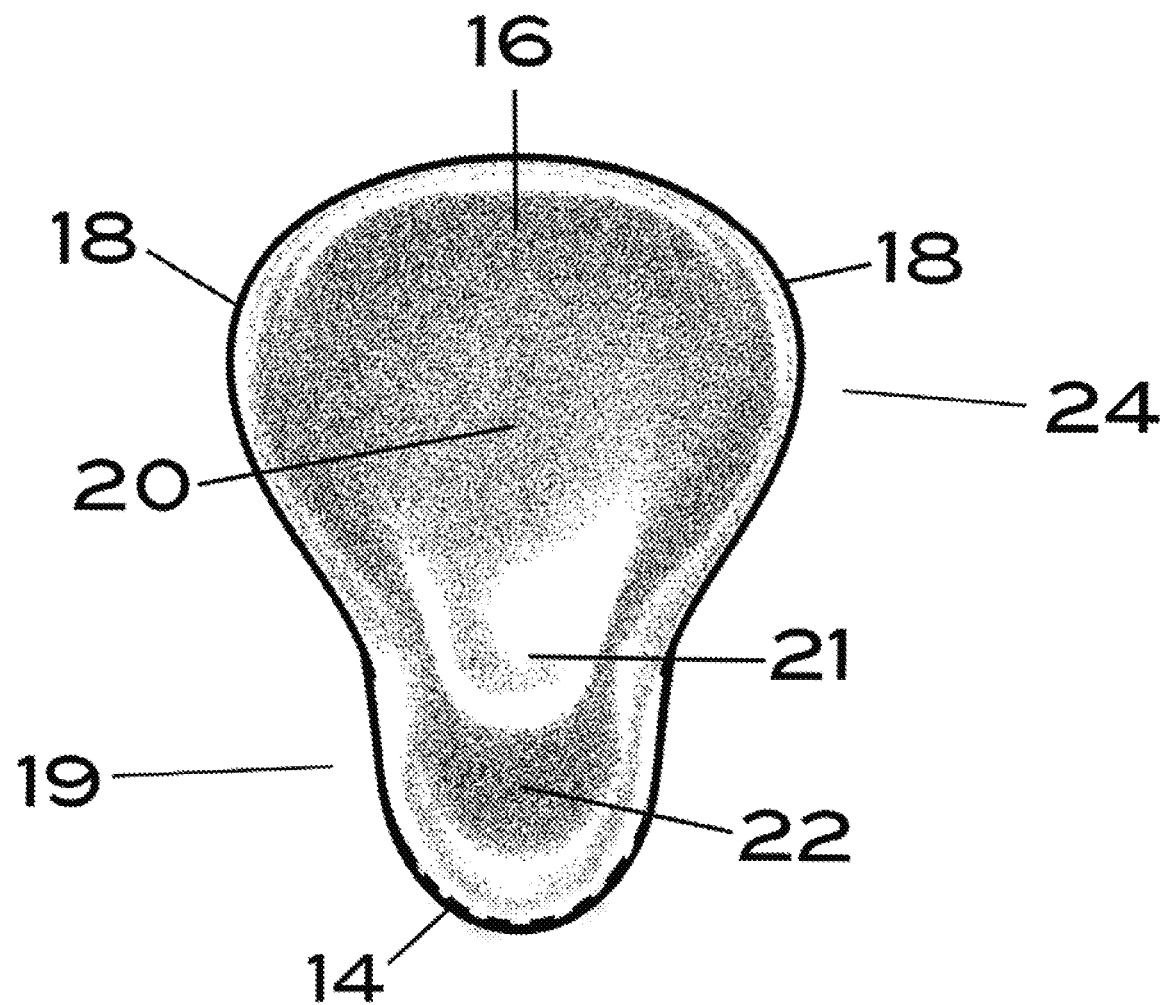
FIG. 5 illustrates a rear view of a genital cover, according to an aspect of the present disclosure.
Figure 9:
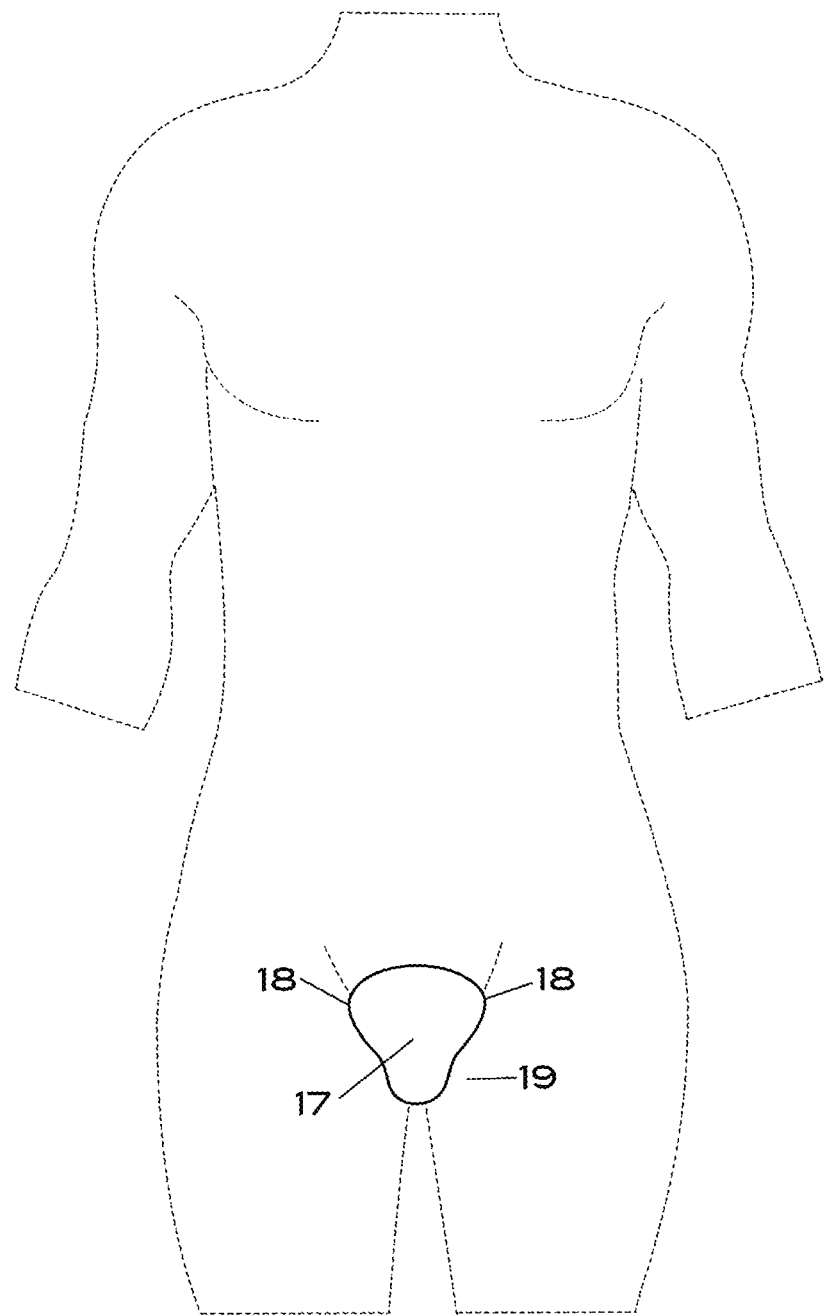
FIG. 9 illustrates a front side view of a genital cover, showing its intended position when worn by a transgender man, according to an aspect of the present disclosure.
Figure 10:
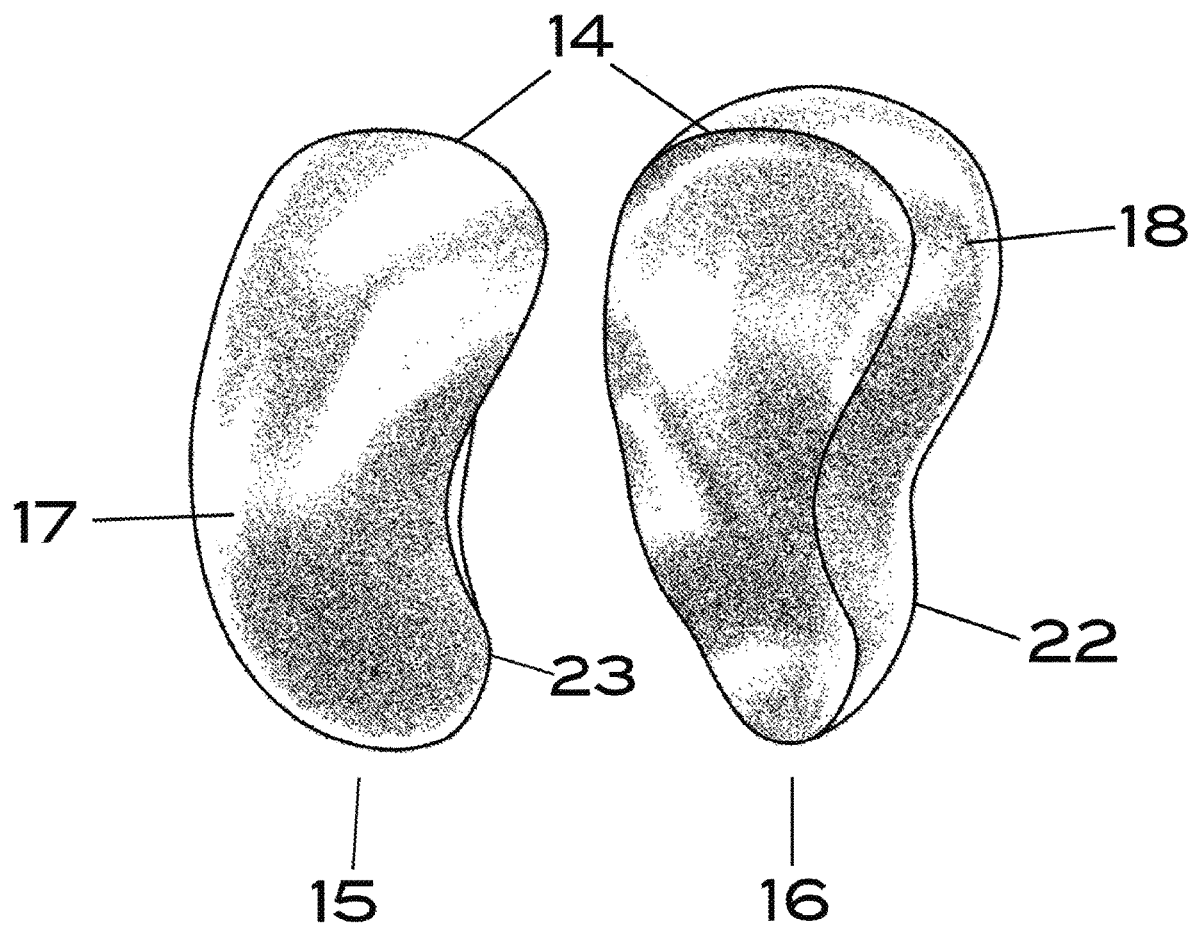
FIG. 10 illustrates a perspective view of a genital cover before assembly, according to an aspect of the present disclosure.

Also, as shown in FIGS. 1-9, the cover may be designed with smooth, rounded edges of the genital cover, which is preferable to allow for maximum comfort to the wearer in all situations where an edge of the genital cover, such as the bilateral outward extending edges 18, compress against the legs during movement as shown in FIG. 9. In some embodiments, the lower extending portion 19 as shown in FIGS. 4 and 5 may be not as wide as the upper portion 24 of the genital cover, as to not impede the forward movement of the legs. The width of lower extending portion 19 may also appropriately emulate the contours of the clothed male external genitalia. The thin concave depression 21 in FIG. 5 may be of additional length or depth, which may accommodate the female external genitalia of the wearer.

FIG. 5 illustrates the broad slightly concave area 20 of the rear component, which rests against the mons pubis as shown in FIG. 9, and can be of any width and length to fill this area of the mons pubis and abdomen. In some embodiments, the broad slightly concave area 20 is of adequate width to cover the entire mons pubis, which helps keep the genital cover in place along with the bilateral outward extending edges, which meet the legs and prevent horizontal shifting. See FIG. 9. The broad slightly concave area 20 may be slightly concave with rounded edges to fit ergonomically to the wearer's body when wearing the cover, as shown in FIG. 8.

Figure 11:
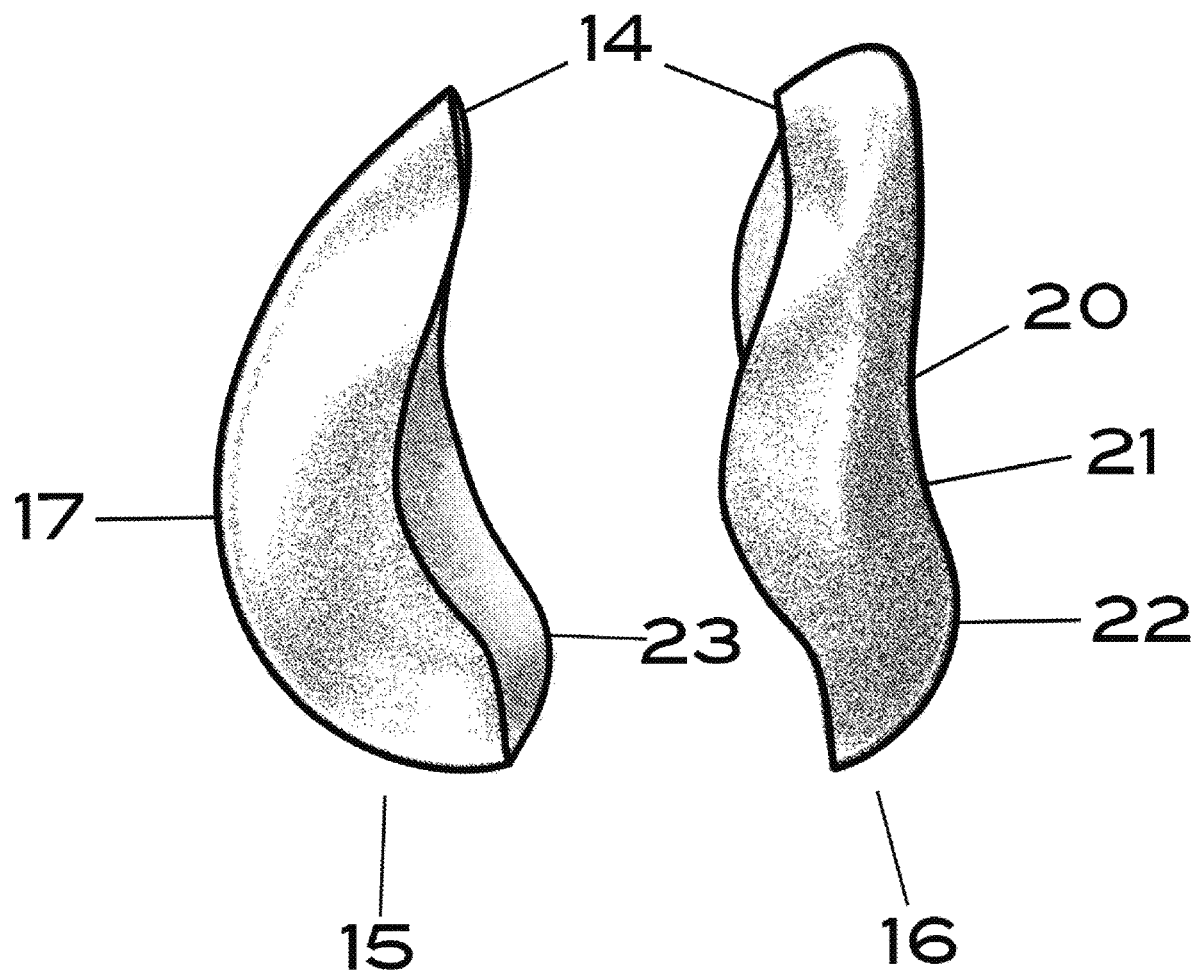
FIG. 11 illustrates a right side view of a genital cover before assembly, according to an aspect of the present disclosure.
Figure 12:
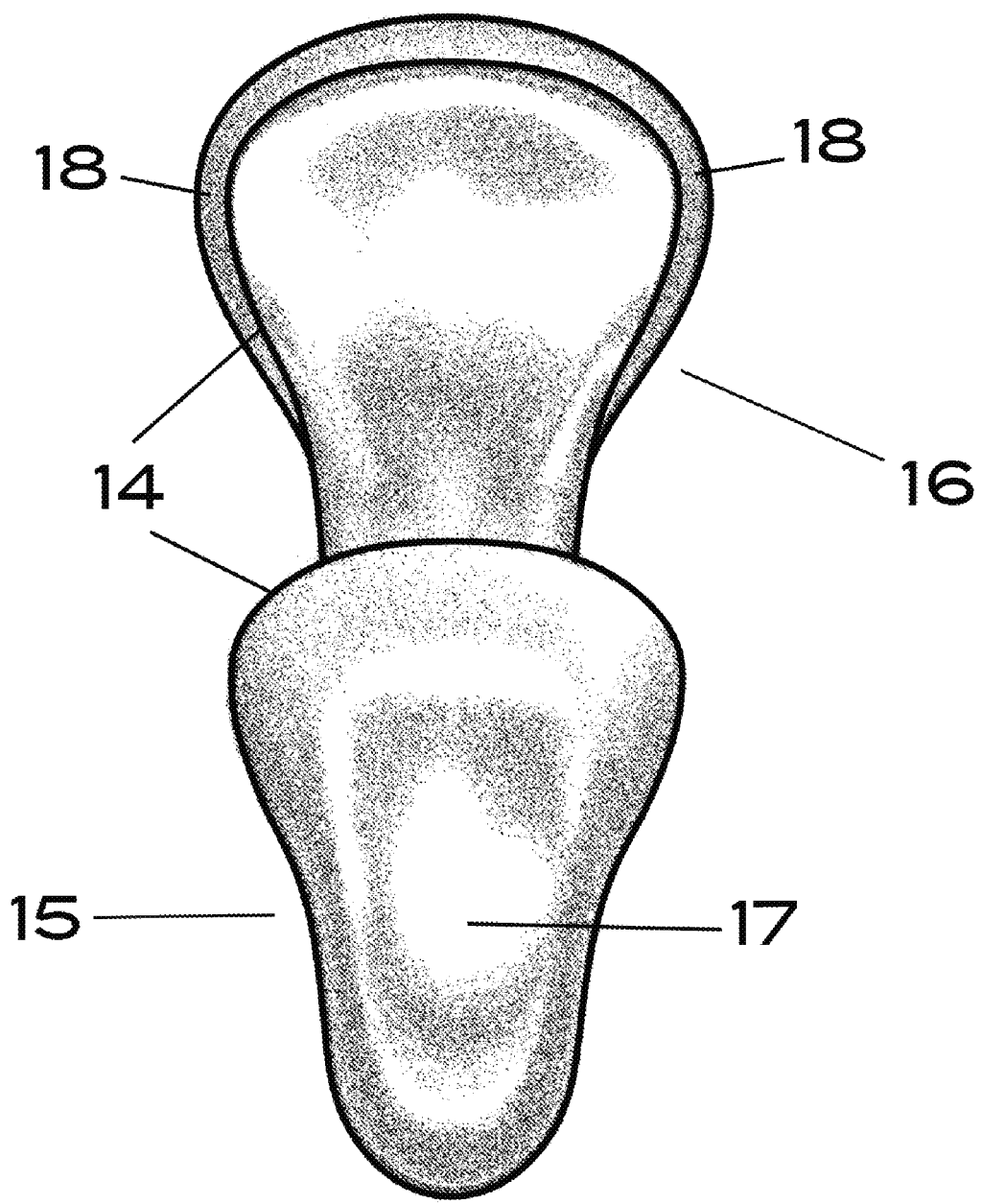
FIG. 12 illustrates a front side view of a genital cover before assembly, according to an aspect of the present disclosure.
Figure 13:
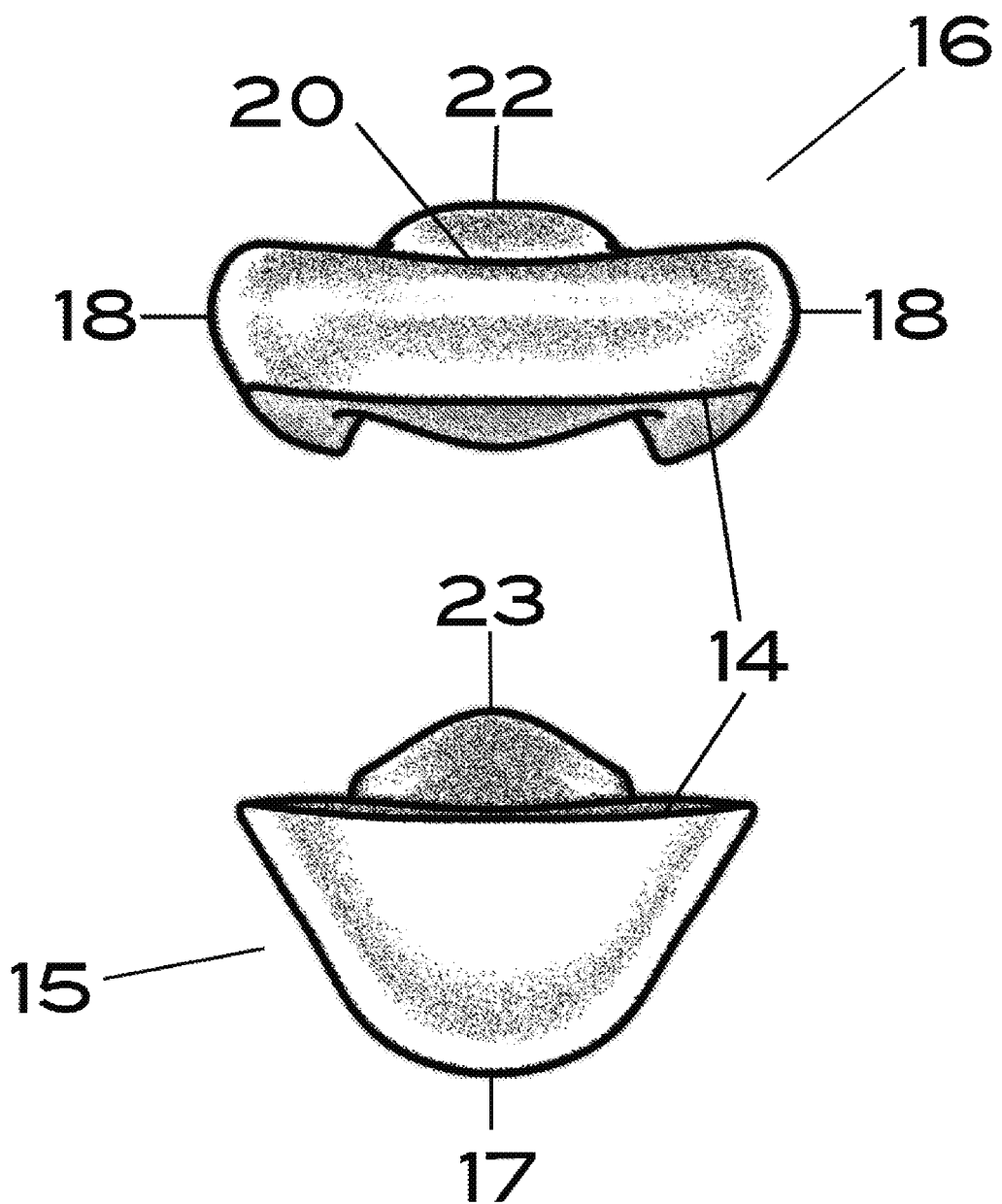
FIG. 13 illustrates a top side view of a genital cover before assembly, according to an aspect of the present disclosure.

As shown in FIG. 8, the bulbous protrusion 22 on the posterior side of the rear component extends along the lower curve of the mons pubis and genital region to provide sufficient resistance to upward movement when force is exerted on the cover from below. In some embodiments, the bulbous protrusion 22 does not extend underneath the genital region. In FIGS. 11 and 13, the inner rear side of front component 15 is visible, showing a bulbous protrusion 23 on the posterior side of the front component 15, which is similar in appearance and function to bulbous protrusion 22, provides additional resistance to upward movement when rear component 16, being comprised of a softer material than front component 15, is compressed to such an extent that bulbous protrusion 22 is unable to provide sufficient resistance to upward movement. This bulbous protrusion 23 may be bigger or smaller than bulbous protrusion 22, so long as it remains hidden when front component 15 and rear component 16 of the genital cover are combined.

FIG. 4 depicts the cover in a general upside down triangular shape. In some embodiments, however, the components described herein can be arranged in a variety of shapes with the same resulting appearance of the wearer possessing male external genitalia, while still retaining good stability.

Figure 6:
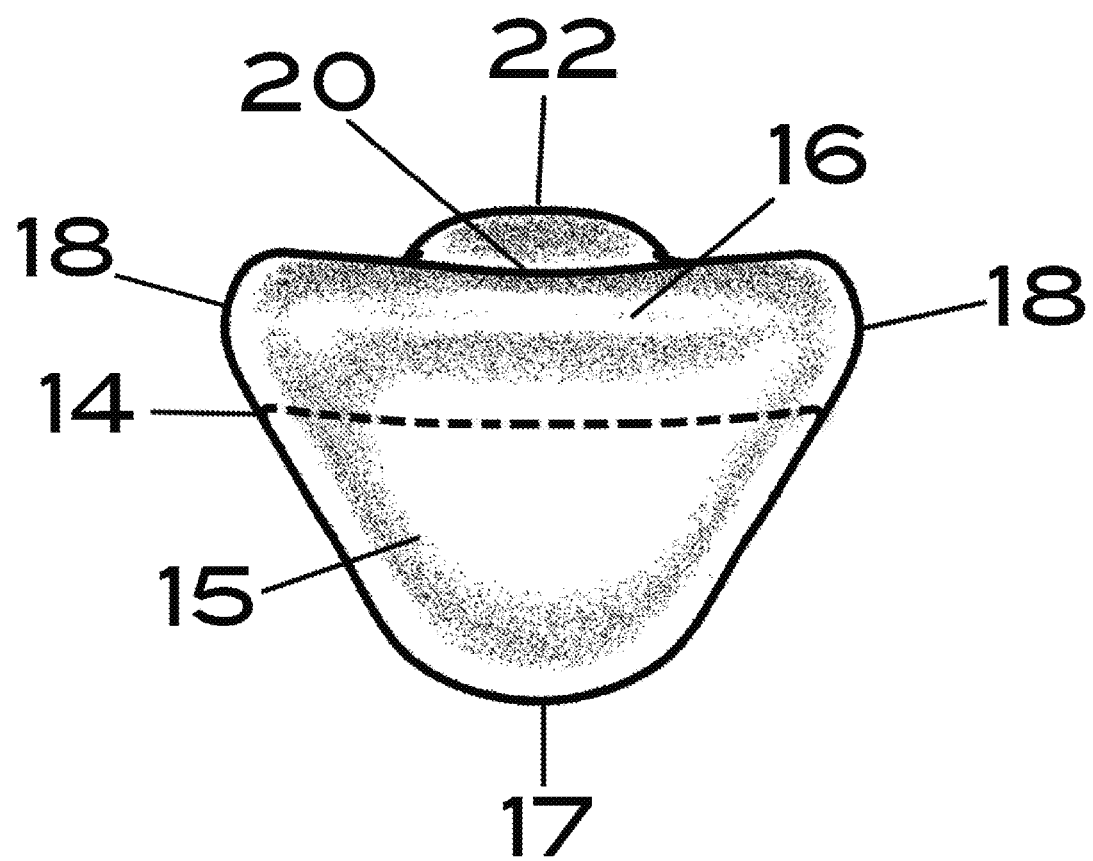
FIG. 6 illustrates a top side view of a genital cover, according to an aspect of the present disclosure.
Figure 7:
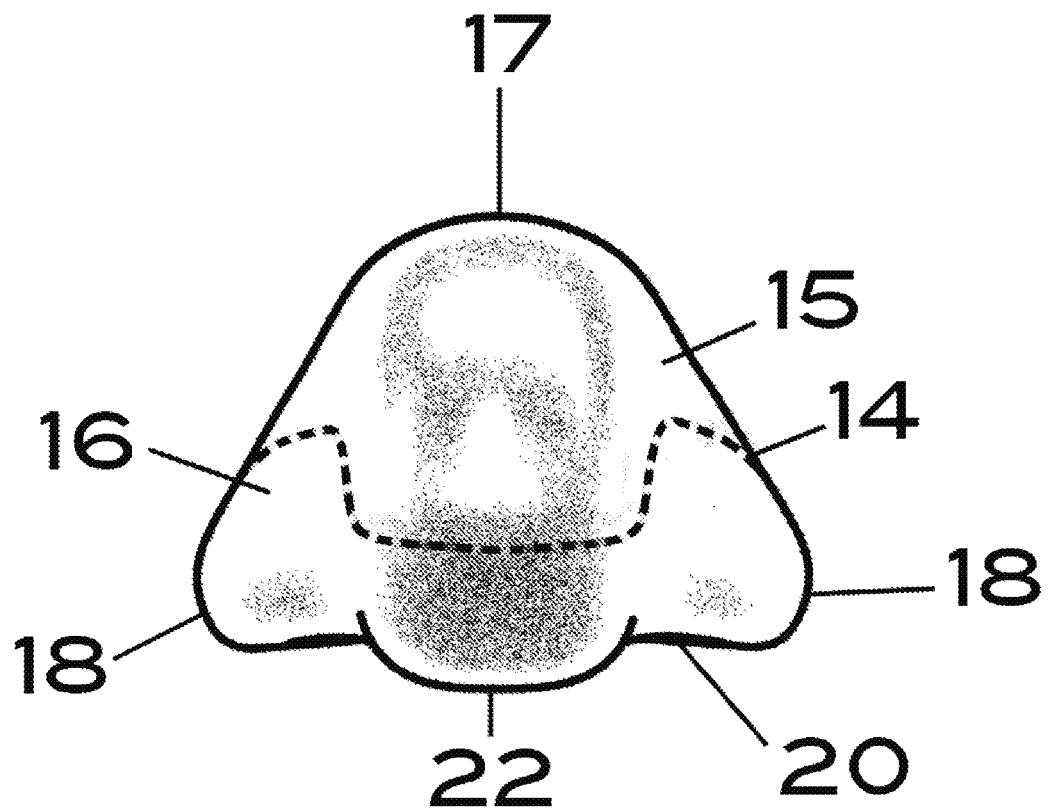
FIG. 7 illustrates a bottom side view of a genital cover, according to an aspect of the present disclosure.

As shown in FIG. 6, the outward extending volume 17 of the front surface may be of adequate distance from the slightly concave area 20 of the rear surface, so as to give the impression that the wearer possesses male external genitalia. This distance may be of any value to accommodate the wearer's preferences, which may be the subtle appearance of the wearer possessing male external genitalia as shown in FIG. 8. In some embodiments, however, the distance may be of a value that results in a less subtle appearance of the wearer possessing male external genitalia.

A depicted in FIGS. 1-13, the cover may include a smooth outer surface. That is, both the concave front surface and the ergonomic rear surface may have a smooth texture. For example, the texture may be smooth enough so that is unnoticeable to the eye when worn underneath a single layer of fabric, such as the underwear. The texture may also be selected so that it is not irritating to the surrounding skin. In some embodiments, the texture may be selected to modify the adherence of the cover to the wearer's garments. For example, the surface may be rough to better adhere to the wearer's garments, or to increase the ability for the cover to stay in place. In some embodiments, the materials of the front and rear surfaces may be selected to that one surface is more or less smooth or rough than the other, in accordance with the wearer's preferences, or to accommodate different garment materials.

In some embodiments, the front component 15 and the rear component 16 are substantially solid. In other embodiments, the front component 15 and the rear component 16 may include one or more hollow spaces within their respective parts. These hollow spaces may improve the performance of the cover by reducing its weight, but should be selected as to still enable varying levels of compression when the cover experiences an external force.

In some embodiments, the cover is a multi-component device including a front component and a rear component, where the front component and rear component are not permanently combined, thereby enabling the components to be replaceable. For example, the front component may be exchanged to account for different garment and fabric types of the wearer's clothing, or for the wearer's preference of the size and shape of the convex outward extension volume.

It should be understood that arrangements described herein are for purposes of example only. As such, those skilled in the art will appreciate that other arrangements and other elements can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

The invention claimed is:

1. A genital cover device, comprising:
 a front component including a substantially convex front surface on an anterior side of the front component and a slightly concave back surface on a posterior side of the front component, wherein the substantially convex front surface includes a convex outward extending volume;
 a rear component including an ergonomic rear surface, wherein the ergonomic rear surface comprises a depression adjacent to a bulbous protrusion on a lower part of a posterior side of the rear component configured to allow the ergonomic rear surface to fit ergonomically against female external genitalia of a user when in use; and
 wherein the slightly concave back surface on the posterior side of the front component is in contact with an anterior side of the rear component.

2. The genital cover device of claim 1, wherein the genital cover device comprises a single unit comprising both the front component and the rear component.

3. The genital cover device of claim 1, wherein the front component is removably coupled to the rear component.

4. The genital cover device of claim 1, wherein the front component comprises a first material, and wherein the rear component comprises a second material that is different than the first material.

5. The genital cover device of claim 4, wherein the first material is denser than the second material.

6. The genital cover device of claim 1, wherein the convex outward extending volume of the substantially convex front surface is sized to simulate male external genitalia.

7. The genital cover device of claim 1, wherein the front component further comprises a lower extending portion and an upper portion, wherein the upper portion is wider than the lower extending portion.

8. The genital cover device of claim 1, wherein the rear component further comprises a slightly concave area on the posterior side of the rear component configured to rest against the mons pubis of the user when in use.

9. The genital cover device of claim 8, wherein the slightly concave area has a width sufficient to cover the entire mons pubis of the user when in use.

10. The genital cover device of claim 1, wherein the rear component further comprises bilateral outward extending edges configured to compress against the legs of the user during movement.

11. The genital cover device of claim 1, wherein the bulbous protrusion on a lower part of the posterior side of the rear component provides resistance to upward movement when force is exerted on the genital cover device from below.

12. The genital cover device of claim 1, wherein the front component further comprises a bulbous protrusion on a lower part of the posterior side of the front component to provide additional resistance to upward movement when force is exerted on the genital cover device from below.

13. The genital cover device of claim 1, wherein an entirety of a posterior side of the front component contact an entirety of an anterior side of the rear component to form the genital cover device.

* * * * *